(12) United States Patent
Bandera et al.

(10) Patent No.: US 12,048,783 B2
(45) Date of Patent: Jul. 30, 2024

(54) 2,4-DISUBSTITUTED PYRIDINES AS MALODOR COUNTERACTING INGREDIENTS

(71) Applicant: FIRMENICH SA, Meyrin (CH)

(72) Inventors: Monica Bandera, Meyrin (CH); Sanja Fitzgerald, Meyrin (CH); Yang Huang, Shanghai (CN); Matthew Rogers, Plainsboro, NJ (US); Ben Smith, Plainsboro, NJ (US)

(73) Assignee: FIRMENICH SA, Satigny (CH)

( * ) Notice: Subject to any disclaimer, the term of this patent is extended or adjusted under 35 U.S.C. 154(b) by 0 days.

(21) Appl. No.: 16/628,120

(22) PCT Filed: Jul. 5, 2018

(86) PCT No.: PCT/EP2018/068228
§ 371 (c)(1),
(2) Date: Jan. 2, 2020

(87) PCT Pub. No.: WO2019/008089
PCT Pub. Date: Jan. 10, 2019

(65) Prior Publication Data
US 2021/0145998 A1  May 20, 2021

Related U.S. Application Data

(60) Provisional application No. 62/529,050, filed on Jul. 6, 2017.

(30) Foreign Application Priority Data

Oct. 25, 2017 (EP) .................................. 17198387

(51) Int. Cl.
*A61L 9/01* (2006.01)
*A01N 43/40* (2006.01)
*A61K 8/49* (2006.01)
*A61Q 15/00* (2006.01)

(52) U.S. Cl.
CPC ............... *A61L 9/01* (2013.01); *A01N 43/40* (2013.01); *A61K 8/4926* (2013.01); *A61Q 15/00* (2013.01); *A61L 2209/21* (2013.01)

(58) Field of Classification Search
CPC ........................................................ A61L 9/01
See application file for complete search history.

(56) References Cited

U.S. PATENT DOCUMENTS

| | | | |
|---|---|---|---|
| 5,538,719 A | 7/1996 | Preti et al. | |
| 8,652,452 B2* | 2/2014 | Delort | A61K 8/00 424/65 |
| 2003/0104969 A1* | 6/2003 | Caswell | C11D 17/042 510/513 |

FOREIGN PATENT DOCUMENTS

| | | |
|---|---|---|
| WO | 2012054527 A2 | 4/2012 |
| WO | 2014210585 A2 | 12/2014 |
| WO | 2018024886 A2 | 2/2018 |

OTHER PUBLICATIONS

Charles Patrick Davis, Normal Flora—Medical Microbiology—NCBI Bookshelf, 1996 (Year: 1996).*
Arshamian et al, The perception of odor pleasantness is shared across cultures, Current Biology 32, 2061-2066, publication date: May 9, 2022 (Year: 2022).*
Gregory Leonardos et al, Odor Threshold Determinations of 53 Odorant Chemicals, Journal of the Air Pollution Control Association, vol. 19, No. 2, Feb. 1969 (Year: 1969).*
Lin et al., Environ. Sci. Tech., 2013, 47(14), pp. 7876-7882.
International Search Report and Written Opinion for International Patent Application No. PCT/EP2018/068228, mailed Sep. 7, 2018, 13 pages.

* cited by examiner

*Primary Examiner* — Mark V Stevens
*Assistant Examiner* — Alparslan Asan
(74) *Attorney, Agent, or Firm* — Armstrong Teasdale LLP

(57) ABSTRACT

The invention relates to malodor masking compositions and/or ingredients, methods for counteracting or masking malodors, and perfuming compositions having odor masking properties comprising 2, 4-dialkyl substituted pyridines for formula (I).

5 Claims, 7 Drawing Sheets

2,4-DISUBSTITUTED PYRIDINES AS MALODOR COUNTERACTING INGREDIENTS

CROSS REFERENCE TO RELATED APPLICATIONS

The present application is a national stage application of International Patent Application No. PCT/EP2018/068228, filed Jul. 5, 2018, which claims priority to U.S. Provisional Patent Application Serial No. 62/529,050, filed on Jul. 6, 2017, and European Patent Application Serial No. 17198387.7, filed on Oct. 25, 2017, the entire contents of which are hereby incorporated by reference in their entirety.

FIELD OF THE INVENTION

The present disclosure relates to the field of perfumery. More particularly, it concerns malodor masking compositions and/or ingredients, methods for counteracting or masking malodors, and perfuming compositions having odor masking properties.

BACKGROUND

Malodorous smells exist in many environments and are experienced in our day life. Such odors are created in any environment. Malodorous smells include the commercial and residential environment malodors generated by, for example, waste products, trash receptacles, toilets, cat litter, and food handling and processing. Other examples include environmental sources, such as bathroom (including feces or urine), laundry, kitchen and body malodors. Malodors are frequently complex mixtures of more than one malodorant compound which may typically include various amines, thiols, sulfides, short chain aliphatic and olefinic acids, e.g. fatty acids, and derivatives thereof. Residential or body related malodors typically include indole, skatole, and methanethiol (found in feces malodor); piperidine and morpholine (found in urine); pyridine and triethyl amine (found in kitchen and garbage malodors); and short chain fatty acids, such as 3-methyl-3-hydroxyhexanoic acid, 3-methylhexanoic acid or 3-20 methyl-2-hexenoic acid, (found in axilla malodors).

Malodors are not pleasant for humans and therefore there is a constant need for malodor counteracting (MOC) solutions decreasing or suppressing the perception of malodors. Various approaches exist to achieve such goal with MOC compositions, and include: masking, which relates to suppression or decrease of the perception of a malodor by various mechanism such as a receptor antagonist activity; and/or suppression, which consists in either suppressing or decreasing the perception by just chemically or physically eliminating the malodor or its generation (e.g. by having an antimicrobial activity).

SUMMARY

One aspect provides a method of treating, reducing, decreasing, modifying, or suppressing malodor, comprising treating a malodor source with a compound of formula (I) in an amount sufficient to inhibit the growth of at least one bacterium selected from the group consisting of S. aureus, S. haemolyticus, and E. coli,

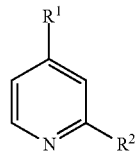

in the form of any one of its stereoisomers or a mixture thereof,
wherein $R^1$ represents a $C_{1-3}$ alkyl group, and
$R^2$ represents a $C_{4-9}$ linear alkyl group; and the compound has between 10 and 15 carbon atoms.

In one aspect, $R^1$ represents a linear $C_{1-3}$ alkyl group.
In one aspect, $R^2$ represents a $C_{5-8}$ linear alkyl group.
In one aspect, the compound of formula (I) is selected from the group consisting of 4-methyl-2-pentyl-pyridine, 4-n-propyl-2-pentyl-pyridine, and 4-ethyl-2-hexyl-pyridine.

In one aspect, the compound of formula (I) is 4-methyl-2-pentyl-pyridine.

In one aspect, the inhibition of the growth of at least one bacterium selected from the group consisting of S. aureus, S. haemolyticus, and E. coli, is sufficient to modify, suppress, reduce, decrease or mask the sensory perception of the malodor source.

In one aspect, the malodor source is selected from the group consisting of kitchen, laundry, bathroom, tobacco, pet, and body malodor.

In one aspect, the amount sufficient to inhibit the growth of at least one bacterium selected from the group consisting of S. aureus, S. haemolyticus, and E. coli is from 300 to 1000 ppm.

One aspect provides a method of reducing, preventing, or inhibiting a subject's perception of malodor, comprising contacting the subject with a compound of formula (I) in an amount sufficient to reduce, prevent, or inhibit the subject's perception of malodor,

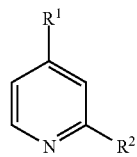

in the form of any one of its stereoisomers or a mixture thereof,
wherein $R^1$ represents a $C_{1-3}$ alkyl group, and
$R^2$ represents a $C_{4-9}$ linear alkyl group; and the compound has between 10 and 15 carbon atoms.

In one aspect, $R^1$ represents a linear $C_{1-3}$ alkyl group.
In one aspect, $R^2$ represents a $C_{5-8}$ linear alkyl group.
In one aspect, the compound of formula (I) is selected from the group consisting of 4-methyl-2-pentyl-pyridine, 4-n-propyl-2-pentyl-pyridine, and 4-ethyl-2-hexyl-pyridine.

In one aspect, the compound of formula (I) is 4-methyl-2-pentyl-pyridine.

In one aspect, the malodor is selected from the group consisting of kitchen, laundry, bathroom, tobacco, pet, and body malodor.

In one aspect, the amount sufficient to reduce, prevent, or inhibit the subject's perception of malodor inhibits an olfactory malodor receptor in the subject.

In one aspect, the amount sufficient to reduce, prevent, or inhibit the subject's perception of malodor is from 10 to 100 ppm.

DETAILED DESCRIPTION

Figure 1A:
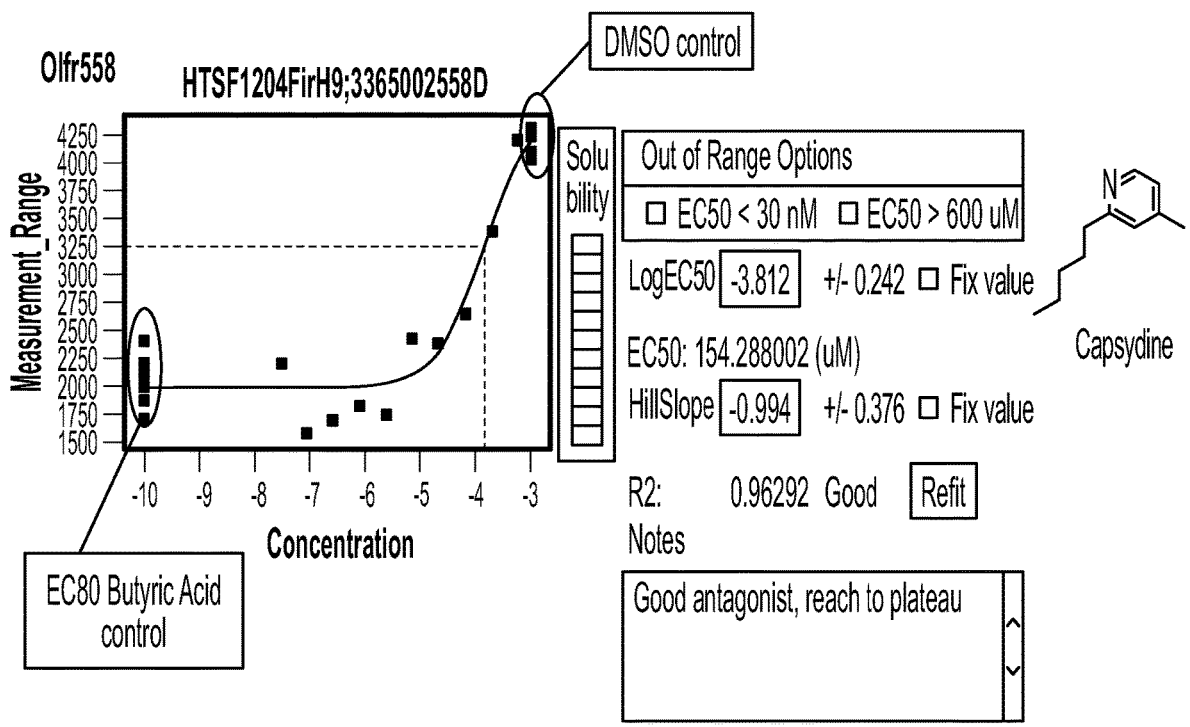
FIG. 1 shows the results of the potency of a compound of formula (I) to inhibit the butyric acid olfactory receptor Olfr558 (panel a), and OR51E1 (panel b).
Figure 1B:
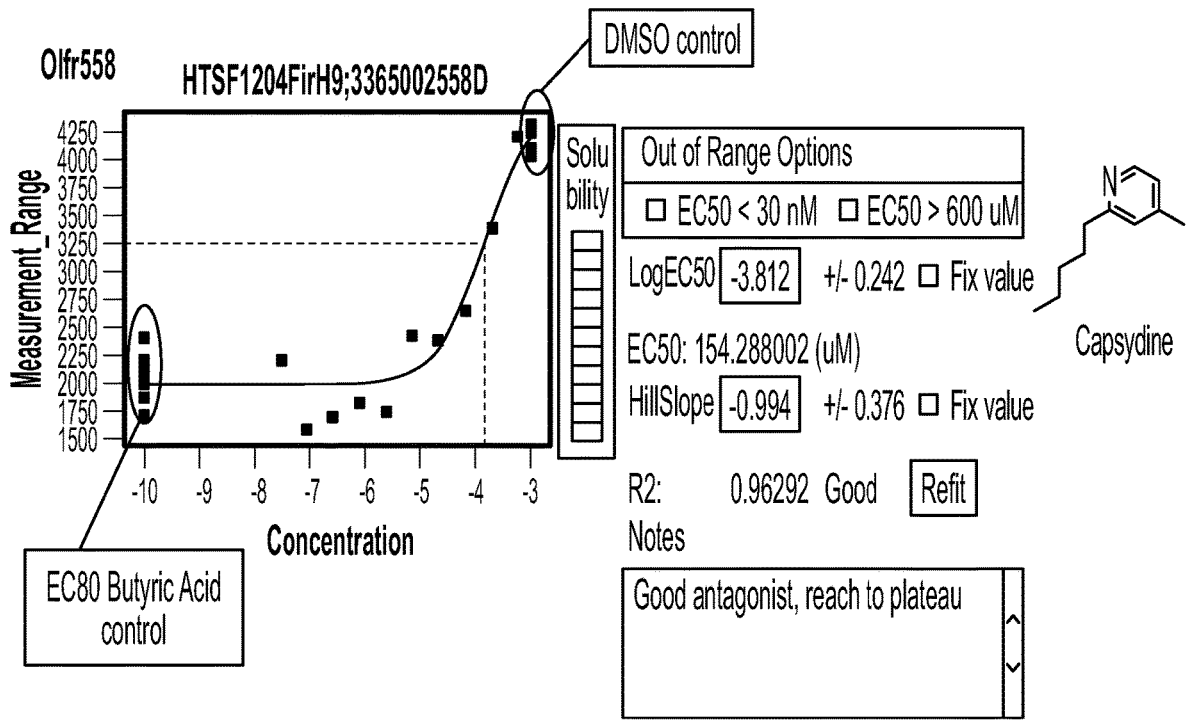
Figure 2A:
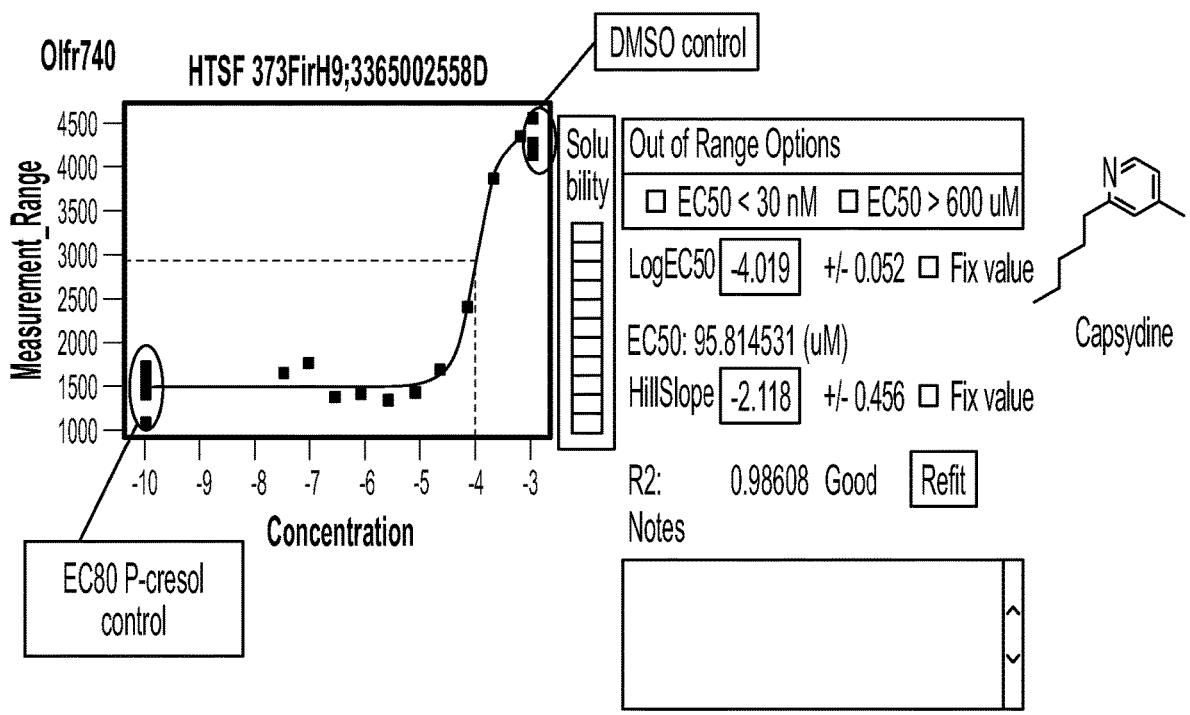
FIG. 2 shows the results of the potency of a compound of formula (I) to inhibit the p-cresol olfactory receptor Olfr740 (panel a), and Olfr742 (panel b).
Figure 2B:
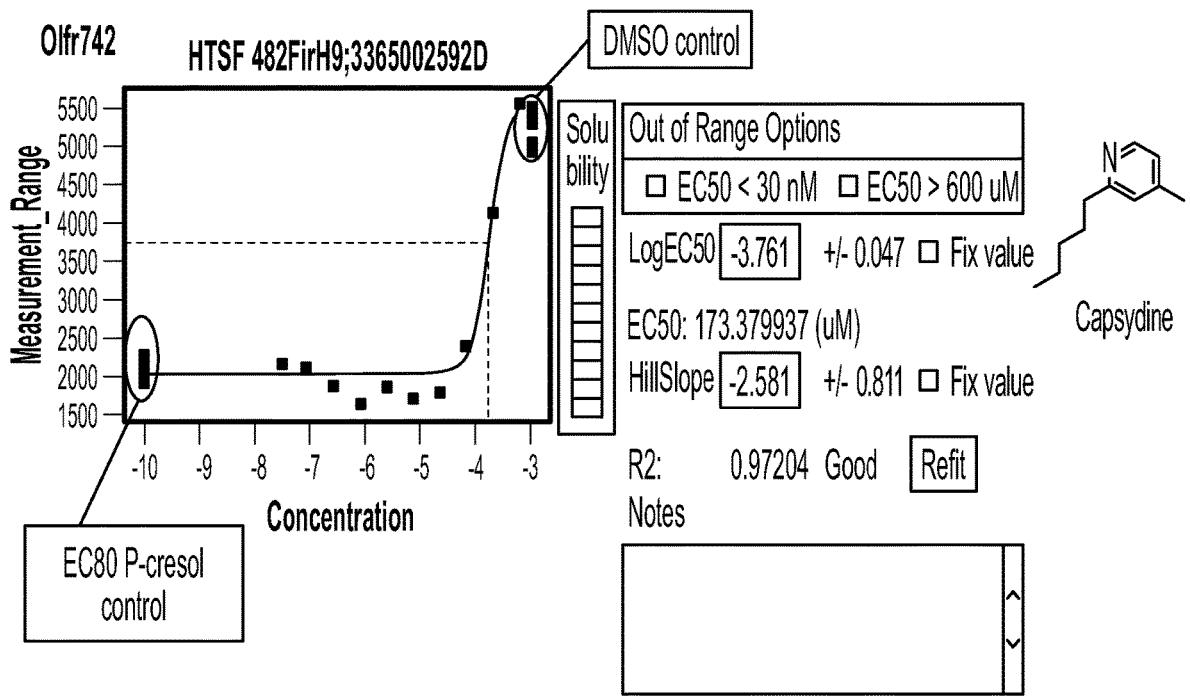
Figure 3:
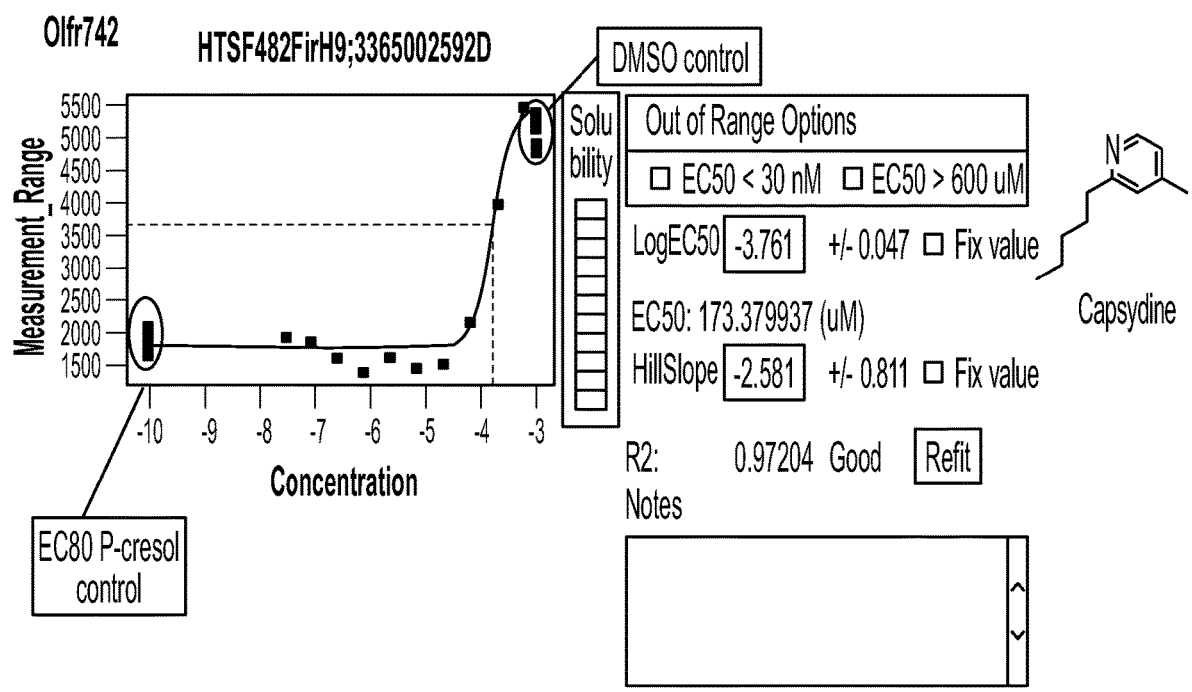
FIG. 3 shows the results of the potency of a compound of formula (I) to inhibit the dimethyl trisulfide (also referred to as DMTS) olfactory receptor OR4S2.

In the following description, reference is made to specific embodiments which may be practiced, which is shown by way of illustration. These embodiments are described in detail to enable those skilled in the art to practice the invention described herein, and it is to be understood that other embodiments may be utilized and that logical changes may be made without departing from the scope of the aspects presented herein. The following description of example embodiments is, therefore, not to be taken in a limited sense, and the scope of the various aspects presented herein is defined by the appended claims.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

Some aspects described herein concern the use of a compound of formula (I) as a MOC ingredient to modify, suppress, reduce, decrease or mask a malodor such as body, laundry, residential and/or pet malodor, which method comprises the step of releasing into the air, or over a surface or the malodor source, an effective amount a compound of formula (I):

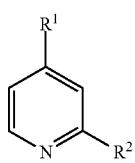

(I)

in the form of any one of its stereoisomers or a mixture thereof,
wherein $R^1$ represents a $C_{1-3}$ alkyl group, and
$R^2$ represents a $C_{4-9}$ linear alkyl group; and the compound has between 10 and 15 carbon atoms.
In some aspects, $R^1$ represents a linear $C_{1-3}$ alkyl group.
In some aspects, $R^2$ represents a $C_{5-8}$ linear alkyl group.

In some aspects, the compound of formula (I) is selected from the group consisting of 4-methyl-2-pentyl-pyridine, 4-n-propyl-2-pentyl-pyridine, and 4-ethyl-2-hexyl-pyridine.

In some aspects, the compound of formula (I) is 4-methyl-2-pentyl-pyridine.

Without intending to be limited to any particular theory, the effective amount of a compound of formula (I) modifies, suppresses, reduces, decreases or masks the malodor by either (i) suppression of the malodor by inhibiting the growth of bacteria and/or (ii) decreasing, suppressing, reducing, or inhibiting a subject's perception of the malodor by antagonizing an olfactory malodor, thereby inhibiting the relevant malodor olfactory receptor or relevant malodor olfactory receptors.

Non-limiting examples of kitchen malodor include any type of malodor present in a residential or commercial kitchen including, but not limited to: kitchen garbage odors that may result from the disposal of raw or cooked meat, fish, vegetables, fruit and/or dairy products; odors experienced during food preparation, especially odors generated from raw fish, raw garlic and raw onions; cooking odors, especially odors produced when cooking meat, fish, onion and/or garlic; the odor of cooking oil used for frying foods; burnt odors that may originate from the over-cooking or burning of foods; odors originating from the kitchen sink drain; odors originating from in-sink disposal units; and, odors originating from a refrigerator.

Non-limiting examples of bathroom malodor include any malodor type of malodor present in a residential or public bathroom/restroom including, but not limited to: odors present immediately after the use of the toilet; lingering toilet odors; stale urine odor; and, moldy or musty odors that often originate in damp areas of the bathroom such as around the bath or shower.

Non-limiting examples of tobacco odor include the odor generated during smoking of cigarettes, cigars or tobacco pipes, or the stale smoke odor that lingers after use of tobacco products in a room, or the odor originating from an ash tray that comprises debris from cigarettes, cigars or tobacco pipes.

Non-limiting examples of pet odor include any type of odor associated with a domestic pet, especially a cat or a dog, and includes, but is not limited to: fecal odors from litter boxes; urine odors from litter boxes; lingering urine odors; wet-dog odor; and, pet-bed odor.

Non-limiting examples of body malodor include any type of odor produced by the human body including, but not limited to: axillary (armpit) odor, scalp odor, foot odor and vaginal odor. "Body malodor" may also mean an odor that originates on the human body and is transferred to another substrate such as a textile; this may include, for example, the odor of worn socks, or the odor of worn sportswear.

Non-limiting examples of laundry malodor include soils such as those found on mechanics' clothes; food handlers, especially butchers' and kitchen workers' clothes; sewer workers' clothes; bar tenders' clothes; fire fighters' clothes; farm clothes; athletic clothing; factory workers' clothes; heavy machinery operators' clothes, and the like.

The reduction of the malodor may be achieved via the application of any known consumer product relevant for the targeted surface. As used herein, the term "surface" refers to the skin, a bathroom, a toilet, a kitchen surface (e.g. a trash) or a fabric (like clothing, bed sheets, carpet, a sofa or a curtain).

It is understood by a person skilled in the art that the compound of formula (I), as defined herein, may be added into composition described herein in neat form, or in a solvent. Alternatively, the compound of formula (I) may first be modified, for example by entrapped with an entrapment material such as for example polymers, capsules, microcapsules, nanocapsules, liposomes, precursors, film formers, absorbents such as for example by using carbon or zeolites, cyclic oligosaccharides and mixtures thereof. Alternatively, the compound of formula (I) may be chemically bound to substrates which are adapted to release the compounds upon application of an exogenous stimulus such as light, enzymes, or the like.

Accordingly, some aspects presented herein provide a composition comprising:
  a. a compound of formula (I);
  b. at least one ingredient selected from the group consisting of a perfumery carrier and a perfumery base; and
  c. optionally at least one perfumery adjuvant.

As used herein, the term "perfumery carrier" refers to a material which is practically neutral from a perfumery point of view, i.e. which does not significantly alter the organoleptic properties of perfuming ingredients. The perfumery carrier may be a liquid or a solid.

Non-limiting examples of liquid perfumery carriers include an emulsifying system, i.e. a solvent and a surfactant system, or a solvent commonly used in perfumery. A detailed description of the nature and type of solvents commonly used in perfumery cannot be exhaustive. However, non-limiting examples solvents include dipropyleneglycol, diethyl phthalate, isopropyl myristate, benzyl benzoate, 2-(2-ethoxyethoxy)-1-ethanol or ethyl citrate. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

Non-limiting examples of solid perfumery carriers include absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualität, Behr's Verlag GmbH & Co., Hamburg, 1996. The encapsulation is a well-known process to a person skilled in the art, and may be performed, for instance, using techniques such as spray-drying, agglomeration or yet extrusion; or consists of a coating encapsulation, including coacervation and complex coacervation technique.

As used herein, the term "perfumery base" refers a composition comprising at least one perfuming co-ingredient. A perfuming co-ingredient does not include a compound of formula (I). As used herein, the term "perfuming co-ingredient" refers to compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

As used herein, the term "perfumery adjuvant" refers to an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

In some aspects, the composition further comprises a functional perfume accord. As used herein, the term "functional perfume accord" refers to a mixture of at least two perfuming ingredients which possess malodor counteracting properties. For example, the functional perfume accord may comprise a mixture of at least two perfuming ingredients that have been shown to counteract fecal malodor, using a sensory panel.

Non-limiting examples of perfuming ingredients that may be included as functional perfume accords include ionones, irones, damascones, damascenone, citral, methylcinnamic aldehyde, pelargodienal, orivone, or mixtures thereof.

In some aspects, the composition further comprises a non-functional perfume accord. As used herein, the term "non-functional perfume accord" refers to a mixture of at least two perfuming ingredients which do not possess malodor counteracting properties.

In some aspects, the composition further comprises at least one other MOC compound. As used herein, the term "other MOC compounds" refers to a material which is already known for a MOC activity and is commonly used in the industry for such use. The at least one other MOC compound can be included to further boost, or complement, the MOC activity of the compound of formula (I).

Non-limiting examples of the at least one other MOC compound include antimicrobial agents, malodor absorbers, chemical neutralisers e.g. acid-base reagents, thiol traps, odour blockers, cross-adaptation agents e.g. as disclosed in U.S. Pat. No. 5,538,719 incorporated herein by reference, malodor complexation agents e.g. various cyclodextrins.

Examples of antimicrobial agents include, but are not limited to, metal salts such as zinc citrate, zinc oxide, zinc pyrethiones, and octopirox; organic acids, such as sorbic acid, benzoic acid, and their salts; parabens, such as methyl paraben, propyl paraben, butyl paraben, ethyl paraben, isopropyl paraben, isobutyl paraben, benzyl paraben, and their salts; alcohols, such as benzyl alcohol, phenyl ethyl alcohol; boric acid; 2,4,4'-trichloro-2-hydroxy-diphenyl ether; phenolic compounds, such as phenol, 2-methyl phenol, 4-ethyl phenol; essential oils such as rosemary, thyme, lavender, eugenol, geranium, tea tree, clove, lemon grass, peppermint, or their active components such as anethole, thymol, eucalyptol, farnesol, menthol, limonene, methyl salicylate, salicylic acid, terpineol, nerolidol, geraniol, and mixtures thereof.

Examples of malodor absorbers include, but are not limited to molecular sieves, such as zeolites, silicas, aluminosilcates, and cyclodextrins; and organic absorbents, such as for example, activated charcoal, dried citrus pulp, cherry pit extract, corncob, and mixtures thereof.

In some aspects, compositions described herein may comprise one, or more than one compound of formula (I). Without intending to be limited to any particular theory, a composition comprising more than one compound of formula (I) may enable a person skilled in the art to prepare MOC compositions possessing an activity fine-tuned toward the targeted malodor or source of malodor.

For the sake of clarity, it is also understood that any mixture resulting directly from a chemical synthesis, e.g. a reaction medium without an adequate purification, in which a compound of formula (I) would be involved as a starting, intermediate or end-product could not be considered as a MOC composition according to the present disclosure as far as the mixture does not provide the compound of formula (I) in a suitable form. Thus, unpurified reaction mixtures are generally excluded from the present disclosure unless otherwise specified.

Furthermore, a compound of formula (I) may also be used in any consumer product for which it may be useful to have a MOC activity at least. Consequently, another object of the present disclosure is represented by a MOC consumer product comprising, as an active ingredient, at least one composition, as defined above. It is understood that the MOC consumer product, by its nature can also be a perfuming one.

As used herein, the term "MOC, and optionally perfuming, consumer product" or similar, refers to a consumer product which is expected to deliver at least a MOC effect, and optionally also a pleasant perfuming effect, to the surface to which it is applied (e.g. skin, hair, textile, or home surface, but also air). In other words, a consumer product according to the present disclosure is a perfumed consumer product which comprises the functional formulation, as well as optionally additional benefit agents, corresponding to the desired consumer product, e.g. a detergent or an air freshener, and an effective amount of at least one invention's compound. For the sake of clarity, the consumer product is a non-edible product.

The nature and type of the constituents of the MOC consumer product do not warrant a more detailed description here, which in any case would not be exhaustive, the skilled person being able to select them on the basis of his general knowledge and according to the nature and the desired effect of said product.

Non-limiting examples of suitable perfuming consumer product include:
- a perfume, such as a fine perfume, an Eau de Toilette, a cologne or an after-shave lotion;
- a fabric care product, such as a liquid detergent, a powder detergent, detergent tablets, a detergent bar, a detergent paste, a liquid fabric softener, fabric softener sheets, a fabric scent booster, a laundry pre-treatment, a fabric refresher, an ironing water, a laundry bleach, a carpet powder or a carpet cleaner;
- a hair care product, such as a shampoo, a hair conditioner, a hair cream, a hair oil, a hair styling product (such as a spray, mousse or gel), a hair coloration product or a hair permanent wave product;
- a skin care product, such as a face cream, a face lotion, a shaving product (such as a foam, cream, gel or oil), a body and/or hand product (such as a lotion, cream, gel or oil), a skin firming product, a depilatory, a talcum powder, a foot care cream or lotion, baby wipes, cleansing wipes, moisturizer wipes, a sun-protection product (such as a spray, lotion, cream or oil), an after-sun lotion, or a self-tanning product;
- a body deodorant or antiperspirant product, such as a body deodorant spray, a roll-on deodorant, a deodorant stick, a deodorant cream, an antiperspirant spray, an antiperspirant stick, a roll-on antiperspirant liquid, an antiperspirant stick, or an antiperspirant cream;
- a skin-cleansing product, such as a soap bar, a shower gel, a liquid hand soap, a bath foam or an intimate wash product;
- an air freshening product, such as an air freshener spray, a gel air freshener, a liquid-wick air freshener, a solid air freshener comprising a porous substrate (such as a paper or card blotter, a porous ceramic, or a porous plastic), a liquid or gel air freshener comprising a permeable membrane, an electrically operated air freshener, and a dual purpose air freshener/disinfectant spray; and/or
- a surface care product, such as an all-purpose cleaner, a furniture polish, a wood floor cleaner, a window cleaner, a hand dishwashing product (such as a liquid, gel or paste), a machine dishwashing product (such as a powder, liquid, gel, tablet or sachet), a toilet bowl cleaning liquid, an in-cistern toilet cleaner, a toilet rim block, or a toilet rim liquid; a pet-litter.

Some of the above-mentioned MOC consumer products may represent an aggressive medium for the compounds of formula (I), thus it may be necessary to protect the latter from premature decomposition, for example by encapsulation or by chemically bounding it to another chemical which is suitable to release the invention's ingredient upon a suitable external stimulus, such as an enzyme, light, heat or a change of pH.

In some aspects, the composition as defined in any of the above aspect may be absorbed on a porous or non-porous substrate in loose powder or compacted form, the substrate being selected from cellulose (paper/cardboard), vermiculite, other industrial absorbents, perlite, calcium carbonate, pumice, wood, sawdust, ground corn cob, ground rice hull, rice hull ash, biochars, starches, modified starches and mixtures thereof.

Accordingly, in some aspects, the present disclosure provides a perfumed consumer product comprising an effective amount of a compound of formula (I). In some aspects, the perfumed consumer product is selected from the group consisting of: air care products, home care products and laundry care products.

In some aspects, the perfumed consumer product comprising an effective amount of a compound of formula (I) comprises a formulation selected from the group consisting of: aerosol and/or water-based air freshener spray, wick/reed air freshener, liquid electrical (plug-in) air freshener, a solid support air freshener, gel-based air freshener, membrane-containing air freshener, bleaching, cleaning, washing detergent powder, liquid all-purpose cleaner, specialty cleaner and liquid detergent.

It should be appreciated by those skilled in the art that the conception and the specific embodiments disclosed might be readily utilized as a basis for modifying or formulating other formulations for carrying the same purposes of the present invention. It should also be realized by those skilled in the art that such equivalent formulations do not depart from the spirit and scope of the disclosure as set forth herein.

The proportions in which compounds of formula (I) can be incorporated into the various aforementioned products or compositions vary within a wide range of values. These values are dependent on the nature of MOC consumer product and on the desired organoleptic effect as well as the nature of the co-ingredients in a given composition when the compounds of formula (I) are mixed with other ingredients, solvents or additives commonly used in the art.

In general, for example, in the case of perfuming compositions, typical concentrations are in the order of 0.001% to 5% by weight, or even more, of compounds of formula (I), based on the weight of the composition into which they are incorporated. Concentrations lower than these, such as in the order of 0.01% to 100% by weight, can be used when the compositions described herein are incorporated into MOC consumer products, the percentage being relative to the weight of the consumer product.

In particular, the concentration of MOC composition according to the aspects described herein, used in the various aforementioned consumer products varies within a various wide range of values depending on the nature of the consumer product. For instance, a MOC composition according some aspects described herein can be used in a perfume product at a concentration of 0.01% to 50% by weight, alternatively at a concentration of 0.2% to 40% by weight, alternatively at a concentration of 0.5% to 25% by weight. For instance, a MOC composition according to some aspects described herein can be used in a fabric care product at a concentration of 0.01% to 20% by weight, alternatively at a concentration of 0.05% to 10% by weight, alternatively at a concentration of 0.1% to 5% by weight. Yet for instance, a MOC composition according to some aspects described herein can be used in a hair care product at a concentration of 0.01% to 10% by weight, alternatively at a concentration of 0.05% to 5% by weight, alternatively at a concentration of 0.1% to 3% by weight. For instance, a MOC composition according to some aspects described herein can be used in a skin care product at a concentration of 0.01% to 10% by weight, alternatively at a concentration of 0.05% to 5% by weight, most preferably at a concentration of 0.1% to 2.5% by weight. For instance, a MOC composition according to some aspects described herein can be used in a body deodorant or antiperspirant product at a concentration of 0.01% to 10% by weight, alternatively at a concentration of 0.05% to 7% by weight, alternatively at a concentration of 0.1% to 5% by weight. Yet for instance, a MOC composition according to some aspects described herein can be used in a skin cleansing product at a concentration of 0.01% to 5% by weight, alternatively at a concentration of 0.05% to 3% by weight, alternatively at a concentration of 0.1% to 2.5% by weight. For instance, a MOC composition according to some aspects described herein can be used in an air freshening product at a concentration of 0.01% to 100% by weight. For instance, a MOC composition according to some aspects described herein can be used in a surface care product at a concentration of 0.001% to 10% by weight, alternatively at a concentration of 0.01% to 5% by weight, alternatively at a concentration of 0.1% to 2% by weight. Yet, for instance, a MOC composition according to some aspects described herein can be used in a pet-litter product at a concentration of 0.001% to 1% by weight, alternatively at a concentration of 0.005% to 0.5% by weight, alternatively at a concentration of 0.01% to 0.3% by weight.

Anti-Bacterial Compositions and Methods: Some aspects presented herein provide a method of preventing, treating, reducing, decreasing, modifying, or suppressing malodor, comprising treating a malodor source with a compound of formula (I) in an amount sufficient to inhibit the growth of at least one bacterium selected from the group consisting of *S. aureus*, *S. haemolyticus*, and *E. coli*.

In some aspects, the term "treating" refers to contacting a surface of a malodor source with a composition comprising a compound of formula (I) as described herein, wherein the contacting results in an effective amount of the compound of formula (I) being deposited on the surface. A composition comprising a compound of formula (I) as described herein may be contacted on a surface by any method readily selected by one of ordinary skill in the art. Examples include, but are not limited to, a spray, a wipe, a solution, and the like.

Alternatively, in some aspects, the term "treating" refers to dispensing or dispersing a composition comprising a compound of formula (I) as described herein into a volume in need thereof. Dispersion or dispensing of the compound of formula (I) as described herein may be achieved by any method readily selected by one of ordinary skill in the art. Examples include, but are not limited to, a spray, a nebulizer, evaporation of a solution containing a compound of formula (I) as described herein, and the like.

Accordingly the present disclosure contemplates formulating a composition comprising a compound of formula (I) as described herein with a suitable carrier to facilitate treating a surface or volume with a composition comprising a compound of formula (I) as described herein to the subject.

In some aspects, the present disclosure provides a perfumed consumer product comprising a compound of formula (I) an in an amount sufficient to inhibit the growth of at least one bacterium selected from the group consisting of *S. aureus*, *S. haemolyticus*, and *E. coli*. In some aspects, the perfumed consumer product is selected from the group consisting of: air care products, home care products and laundry care products.

In some aspects, the perfumed consumer product comprising an effective amount of a compound of formula (I) comprises a formulation selected from the group consisting of: aerosol and/or water-based air freshener spray, wick/reed air freshener, liquid electrical (plug-in) air freshener, a solid support air freshener, gel-based air freshener, membrane-containing air freshener, bleaching, cleaning, washing detergent powder, liquid all-purpose cleaner, specialty cleaner and liquid detergent.

In some aspects, the compound of formula (I) is a compound described in U.S. Pat. No. 8,652,452 B2.

In some aspects, the compound of formula (I) is selected from the group consisting of 4-methyl-2-pentyl-pyridine, 4-n-propyl-2-pentyl-pyridine, and 4-ethyl-2-hexyl-pyridine.

In some aspects, the compound of formula (I) is 4-methyl-2-pentyl-pyridine.

Without intending to be limited to any particular theory, malodor, such as for example, human axillary malodor is commonly attributed to the bacterial degradation of precursors. These precursor compounds are transformed by bacteria to release odorant carboxylic acids, sulfur compounds and odorant steroids. Accordingly, in some aspects, the method of preventing malodor comprises reducing the amount of bacteria present, thereby reducing the production of odorant carboxylic acids, sulfur compounds and odorant steroids. In some aspects, inhibiting the growth of the bacteria reduces the amount of bacteria present.

Accordingly, in some aspects, the inhibition of the growth of at least one bacterium selected from the group consisting of *S. aureus*, *S. haemolyticus*, and *E. coli*, is sufficient to prevent, modify, suppress, reduce, decrease or mask the sensory perception of the malodor source.

In some aspects, the malodor source is selected from the group consisting of kitchen, bathroom, laundry, tobacco, pet, and body malodor.

In some aspects, the present disclosure provides a method of inhibiting the growth of at least one bacterium on a surface, the at least one bacterium selected from the group consisting of *S. aureus, S. haemolyticus*, and *E. coli*, comprising treating the surface with a compound of formula (I) in an amount sufficient to inhibit the growth of at least one bacterium,

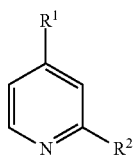

(I)

in the form of any one of its stereoisomers or a mixture thereof,
wherein $R^1$ represents a $C_{1-3}$ alkyl group, and
$R^2$ represents a $C_{4-9}$ linear alkyl group; and the compound has between 10 and 15 carbon atoms.

In some aspects, $R^1$ represents a linear $C_{1-3}$ alkyl group.
In some aspects, $R^2$ represents a $C_{5-8}$ linear alkyl group.
In some aspects, the compound of formula (I) is selected from the group consisting of 4-methyl-2-pentyl-pyridine, 4-n-propyl-2-pentyl-pyridine, and 4-ethyl-2-hexyl-pyridine.

In some aspects, the compound of formula (I) is 4-methyl-2-pentyl-pyridine.

In some aspects, the amount sufficient to inhibit the growth of at least one bacterium selected from the group consisting of *S. aureus, S. haemolyticus*, and *E. coli* is from 300 to 1000 ppm. In some aspects, the amount sufficient to inhibit the growth of at least one bacterium selected from the group consisting of *S. aureus, S. haemolyticus*, and *E. coli* is from 400 to 1000 ppm. In some aspects, the amount sufficient to inhibit the growth of at least one bacterium selected from the group consisting of *S. aureus, S. haemolyticus*, and *E. coli* is from 500 to 1000 ppm. In some aspects, the amount sufficient to inhibit the growth of at least one bacterium selected from the group consisting of *S. aureus, S. haemolyticus*, and *E. coli* is from 600 to 1000 ppm. In some aspects, the amount sufficient to inhibit the growth of at least one bacterium selected from the group consisting of *S. aureus, S. haemolyticus*, and *E. coli* is from 700 to 1000 ppm. In some aspects, the amount sufficient to inhibit the growth of at least one bacterium selected from the group consisting of *S. aureus, S. haemolyticus*, and *E. coli* is from 800 to 1000 ppm. In some aspects, the amount sufficient to inhibit the growth of at least one bacterium selected from the group consisting of *S. aureus, S. haemolyticus*, and *E. coli* is from 900 to 1000 ppm.

In some aspects, the amount sufficient to inhibit the growth of at least one bacterium selected from the group consisting of *S. aureus, S. haemolyticus*, and *E. coli* is from 300 to 900 ppm. In some aspects, the amount sufficient to inhibit the growth of at least one bacterium selected from the group consisting of *S. aureus, S. haemolyticus*, and *E. coli* is from 300 to 800 ppm. In some aspects, the amount sufficient to inhibit the growth of at least one bacterium selected from the group consisting of *S. aureus, S. haemolyticus*, and *E. coli* is from 300 to 700 ppm. In some aspects, the amount sufficient to inhibit the growth of at least one bacterium selected from the group consisting of *S. aureus, S. haemolyticus*, and *E. coli* is from 300 to 600 ppm. In some aspects, the amount sufficient to inhibit the growth of at least one bacterium selected from the group consisting of *S. aureus, S. haemolyticus*, and *E. coli* is from 300 to 500 ppm. In some aspects, the amount sufficient to inhibit the growth of at least one bacterium selected from the group consisting of *S. aureus, S. haemolyticus*, and *E. coli* is from 300 to 400 ppm.

Referring to Example 2 and Table 3 below, the amount of a compound of formula (I) that is effective to inhibit the growth of any one of the bacterial strains *S. aureus, S. haemolyticus*, or *E. coli*, ranged from approximately 400 to 800 ppm in solution.

In some aspects, the inhibition of the growth of at least one bacterium selected from the group consisting of *S. aureus, S. haemolyticus*, and *E. coli* provides an additional benefit. In some aspects, the additional benefit is selected from the group consisting of: reducing fecal contamination of surfaces, treatment of skin infections, and treatment of respiratory infections.

By way of illustration, *E. coli* is present in feces. Accordingly, the methods described herein may reduce fecal contamination of surfaces by inhibiting the growth of *E. coli*, thereby reducing the amount of *E. coli* on the surface.

Similarly, *S. aureus* is a pathogen, and can be responsible for a range of illnesses, from minor skin infections, such as pimples, impetigo, boils, cellulitis, folliculitis, carbuncles, scalded skin syndrome, and abscesses, to life-threatening diseases such as pneumonia, meningitis, osteomyelitis, endocarditis, toxic shock syndrome, bacteremia, and sepsis. Accordingly, the methods described herein may treat a subject suffering a *S. aureus* infection by inhibiting the growth of *S. aureus*, thereby reducing the amount of *S. aureus* at the site of infection.

Olfactory Malodor Receptor Antagonist Compositions and Methods: Some aspects presented herein provide a method of reducing, preventing, or inhibiting a subject's perception of malodor, comprising contacting the subject with a compound of formula (I) in an amount sufficient to reduce, prevent, or inhibit the subject's perception of malodor.

In some aspects, the term "contacting" refers to administering to a subject, a composition comprising a compound of formula (I) as described herein, wherein the administering results in dosing the subject with an effective amount of the compound of formula (I). Administration may be via any method readily selected by one of ordinary skill in the art. Methods include, but are not limited to, topical administration, inhalation, and the like. Accordingly the present disclosure contemplates formulating a composition comprising a compound of formula (I) as described herein with a suitable carrier to facilitate administering the a composition comprising a compound of formula (I) as described herein to the subject.

In some aspects, the present disclosure provides a perfumed consumer product comprising a compound of formula (I) in an amount sufficient to reduce, prevent, or inhibit the subject's perception of malodor. In some aspects, the perfumed consumer product is selected from the group consisting of: air care products, home care products and laundry care products.

In some aspects, the perfumed consumer product comprising an effective amount of a compound of formula (I) comprises a formulation selected from the group consisting of: aerosol and/or water-based air freshener spray, wick/reed air freshener, liquid electrical (plug-in) air freshener, a solid support air freshener, gel-based air freshener, membrane-containing air freshener, bleaching, cleaning, washing detergent powder, liquid all-purpose cleaner, specialty cleaner and liquid detergent.

In some aspects, the compound of formula (I) is a compound described in U.S. Pat. No. 8,652,452 B2.

In some aspects, the compound of formula (I) is selected from the group consisting of 4-methyl-2-pentyl-pyridine, 4-n-propyl-2-pentyl-pyridine, and 4-ethyl-2-hexyl-pyridine.

In some aspects, the compound of formula (I) is 4-methyl-2-pentyl-pyridine.

In some aspects, the malodor is selected from the group consisting of kitchen, bathroom, tobacco, pet, laundry, and body malodor.

In some aspects, the amount sufficient to reduce, prevent, or inhibit the subject's perception of malodor is from 10 to 100 ppm.

Without intending to be limited to any particular theory, residential or body related malodors are typically due to various chemical compounds such as indole, skatole, and methanethiol found in feces malodor; piperidine and morpholine found in urine; pyridine and triethyl amine found in kitchen and garbage malodors; and short chain fatty acids, such as 3-methyl-3-hydroxyhexanoic acid, 3-methylhexanoic acid or 3-20 methyl-2-hexenoic acid, found in axillary malodors.

In some aspects, compositions comprising compounds of formula (I) are able to block specific olfactory malodor receptors. In some embodiments, the olfactory malodor receptors are fecal olfactory malodor receptors. Non-limiting examples of fecal olfactory malodor receptors are disclosed in International Patent Application Publication No. WO2014210585.

In some aspects, the fecal malodor olfactory receptor is an indole malodor olfactory receptor. In some aspects, the indole malodor olfactory receptor is selected from the group consisting of olfr558 and OR51E1.

In some aspects, the fecal malodor olfactory receptor is a dimethyl trisulfide (also referred to as DMTS) olfactory malodor receptor. In some aspects, the DMTS malodor olfactory receptor is OR4S2.

In some aspects, the fecal malodor olfactory receptor is a p-cresol malodor olfactory receptor. In some aspects, the p-cresol malodor olfactory receptor is selected from the group consisting of Olfr742 and Olfr740.

In some aspects, the fecal malodor olfactory receptor is a butyric acid malodor olfactory receptor. In some aspects, the butyric acid malodor olfactory receptor is selected from the group consisting of Olfr742 and Olfr740.

As used herein, "malodor target" is meant to designate a molecular component of malodor characterized in Lin et al, Environ. Sci. Technol., 2013, 47 (14), pp 7876-7882, including indole, butyric acid, p-cresol, skatole, and dimethyl trisulfide.

Accordingly, in some aspects, the present disclosure provides a composition comprising a compound of formula (I), wherein the compound of formula (I) is present in an amount sufficient to reduce, prevent, or inhibit a subject's perception of malodor.

In some aspects, the present disclosure provides a composition comprising a compound of formula (I), wherein the compound of formula (I) is present in an amount sufficient to block a subject's perception of malodor.

In some aspects, the amount sufficient to reduce, prevent, or inhibit the subject's perception of malodor is from 10 to 100 ppm. In some aspects, the amount sufficient to reduce, prevent, or inhibit the subject's perception of malodor is from 20 to 100 ppm. In some aspects, the amount sufficient to reduce, prevent, or inhibit the subject's perception of malodor is from 30 to 100 ppm. In some aspects, the amount sufficient to reduce, prevent, or inhibit the subject's perception of malodor is from 40 to 100 ppm. In some aspects, the amount sufficient to reduce, prevent, or inhibit the subject's perception of malodor is from 50 to 100 ppm. In some aspects, the amount sufficient to reduce, prevent, or inhibit the subject's perception of malodor is from 60 to 100 ppm. In some aspects, the amount sufficient to reduce, prevent, or inhibit the subject's perception of malodor is from 70 to 100 ppm. In some aspects, the amount sufficient to reduce, prevent, or inhibit the subject's perception of malodor is from 80 to 100 ppm. In some aspects, the amount sufficient to reduce, prevent, or inhibit the subject's perception of malodor is from 90 to 100 ppm.

In some aspects, the amount sufficient to reduce, prevent, or inhibit the subject's perception of malodor is from 10 to 90 ppm. In some aspects, the amount sufficient to reduce, prevent, or inhibit the subject's perception of malodor is from 10 to 80 ppm. In some aspects, the amount sufficient to reduce, prevent, or inhibit the subject's perception of malodor is from 10 to 70 ppm. In some aspects, the amount sufficient to reduce, prevent, or inhibit the subject's perception of malodor is from 10 to 60 ppm. In some aspects, the amount sufficient to reduce, prevent, or inhibit the subject's perception of malodor is from 10 to 50 ppm. In some aspects, the amount sufficient to reduce, prevent, or inhibit the subject's perception of malodor is from 10 to 40 ppm. In some aspects, the amount sufficient to reduce, prevent, or inhibit the subject's perception of malodor is from 10 to 30 ppm. In some aspects, the amount sufficient to reduce, prevent, or inhibit the subject's perception of malodor is from 10 to 20 ppm.

In some aspects, the amount sufficient to reduce, prevent, or inhibit the subject's perception of malodor inhibits an olfactory malodor receptor in the subject.

Referring to FIGS. 1 to 4 below, the amount of a compound of formula (I) that is effective to inhibit the activity of malodor olfactory receptors is calculated using the $EC_{50}$ value, as determined using a receptor-based assay. In some aspects, the amount of a compound of formula (I) that is effective to inhibit the activity of malodor olfactory receptors ranges from 10 to 100 ppm in solution.

The present invention is best illustrated but is not limited to the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical shifts δ are indicated in ppm with respect to TMS as standard, the coupling constants J are expressed in Hz.

EXAMPLES

Example 1: MOC Activity of Compounds of Formula (I)

Compounds of formula (I) will be tested, using current sensory analysis methods, for their ability to reduce the perception of bathroom, tobacco, kitchen, pet and body malodors.

Various malodor models will be prepared, by admixing various ingredients as per the below tables, or according to the protocol described:

Bathroom Malodor

| Ingredient | % w/w |
| --- | --- |
| Dipropylene glycol | 62.82 |
| Skatole | 0.91 |
| 2-Naphthalenethiol | 0.91 |
| Thioglycolic acid | 21.18 |
| n-Caproic acid | 6.00 |
| 4-Methylphenyl 3-Methylbutanoate | 2.18 |
| n-Methylmorpholine | 6.00 |
| Total | 100.00 |

Kitchen Malodor

| Ingredient | % w/w |
| --- | --- |
| Diacetyl | 3.85 |
| Pyridine | 3.85 |
| Allyl sulfide | 9.23 |
| Methyl sulfide | 40.00 |
| Heptaldehyde | 3.85 |
| Paraldehyde | 1.90 |
| Propionic acid | 36.92 |
| Acetic acid, glacial | 0.40 |
| Total | 100.00 |

Body Malodor

| Ingredient | % w/w |
| --- | --- |
| n-Caproic acid | 30.00 |
| Isovaleraldehyde | 30.00 |
| Phenylacetic acid | 3.00 |
| Butyric acid | 0.25 |
| Indole | 1.50 |
| p-Cresyl isovalerate | 1.50 |
| p-Cresyl phenyl acetate | 2.75 |
| Thioglycolic acid | 5.00 |
| Dipropylene glycol | 26.00 |
| Total | 100.00 |

Pet Malodor

| Ingredient | % w/w |
| --- | --- |
| Skatole | 0.91 |
| Isovaleric acid | 2.18 |
| Methyl mercaptan (10% w/w in triethylcitrate) | 0.12 |
| Indole (0.5% w/w in Dipropylene glycol) | 1.50 |
| Urea | 1.00 |
| n-Caproic acid | 2.18 |
| Dipropylene glycol | 92.11 |
| Total | 100.00 |

Tobacco malodor will be prepared by extraction of cigarette debris, comprising: ash; filter; and, paper. The debris from 30 smoked Marlboro Red cigarettes (origin: Philip Morris International) will be collected in a 500 ml glass powder jar with a screw closure. 300 ml of ethanol will be added. The combination will be mixed in a Turbula mixer for 8 hours and then filtered through a Whatman Grade 4 filter paper. The filtrate will be used as the tobacco malodor.

The test concentration of the malodor sample used in each case will be selected so as to provide a perceived malodor intensity, when evaluated in Sniffin'Sticks odor pens as described below, approximately of the order of 6 units on the scale described below.

The malodor concentrations that are perceived as comprising a malodor intensity rating of approximately 6 when evaluated in Sniffin'Sticks odor pens are expected to be as follows:
Bathroom malodor: 0.3% by weight in propylene glycol
Kitchen malodor: 30% by weight in propylene glycol
Body malodor: 0.5% by weight in propylene glycol
Pet malodor: 0.5% by weight in propylene glycol
Tobacco malodor: 50% by weight in propylene glycol The test concentration of a compound of formula (I) used in each of the malodor reduction tests will be selected so as to provide a perceived intensity, when evaluated in Sniffin' Sticks odor pens as described below, that was approximately of the order of 6 units on the scale described below.

Stock solutions will be prepared as follows:
Compound of formula (I) 32% by weight: 12.8 g of Compound 1 will be mixed with 27.2 g of propylene glycol.
Bathroom malodor 0.6% by weight: 0.6 g of bathroom malodor will be mixed with 99.4 g of propylene glycol.
Kitchen malodor 60% by weight: 12.0 g of kitchen malodor will be mixed with 8.0 g of propylene glycol.
Body malodor 1% by weight: 1.0 g of body malodor will be mixed with 99.0 g of propylene glycol.
Pet malodor 1% by weight: 1.0 g of pet malodor will be mixed with 99.0 g of propylene glycol.
The tobacco malodor will be used as is.

Each sensory test will comprise 3 samples: a malodor only sample; a test sample comprising a combination of the compound of formula (I) and the test malodor; and, a compound of formula (I) only sample. The samples for the sensory tests will be prepared as follows:

Malodor only sample: in a separate beaker 3.0 g of malodor stock solution will be mixed with 3.0 g of propylene glycol. Once fully homogenized, 2.0 g of the resulting solution will be applied to the absorbent fiber in the body of a Sniffin' Stick odor pen (origin: Burghart Messtechnik GmbH). The odor pen will be immediately capped and allowed to equilibrate for 24 hours before use.

Compound of formula (I) only sample: in a separate beaker 3.0 g of Compound of formula (I) stock solution will be mixed with 3.0 g of propylene glycol. Once fully homogenized, 2.0 g of the resulting solution will be applied to the absorbent fiber in the body of a Sniffin' Stick odor pen (origin: Burghart Messtechnik GmbH). The odor pen will be immediately capped and allowed to equilibrate for 24 hours before use.

Test samples: in a separate beaker 3.0 g of Compound of formula (I) stock solution will be mixed with 3.0 g of malodor stock solution. Once fully homogenized, 2.0 g of the resulting solution will be applied to the absorbent fiber in the body of a Sniffin' Stick odor pen (origin: Burghart Messtechnik GmbH). The odor pen will be immediately capped and allowed to equilibrate for 24 hours before use.

Sensory Test Procedure: The samples will be assessed by a panel of 19 trained panelists. By "trained panelists" it is meant individuals that have previously been screened for olfactive acuity and are experienced in rating the perfume and malodor intensity. Moreover, the panelists are prior acquainted with the malodor sample before carrying out the malodor reduction efficacy test.

Each test will comprise a malodor only sample, a compound of formula (I) only sample, and a test sample that comprises the compound of formula (I) and the malodor.

The samples will be presented to the panelists in Sniffin' Sticks odor pens, prepared according to the description above. Each Sniffin' Stick will be labeled with a randomly generated 3 digit code. Sample presentation will be blind, balanced, randomized and sequential monadic.

After smelling an identified malodor only reference sample first to familiarize themselves with the malodor, the panelists will be asked to rate the malodor intensity and the overall odor intensity of each sample using a linear, labeled line scale, where 0=no odor and 10=extremely strong odor.

The data generated from the panel's evaluations will be statistically analyzed in each case using variance analysis (ANOVA) with Duncan's post-hoc analysis ($\alpha$=0.05).

Example 2: MOC Activity of Compounds of Formula (I) via Odor Suppression and Anti-Bacterial Activity Preparation of bacterial solutions: Bacterial solutions of three bacterial strains were prepared for MIC test as follows. Stock cultures stored at −80° C. were subcultured onto agar plate media, and incubated at 37° C. for 24 h to obtain single colonies. Single colonies of the primary cultures were inoculated into broth media and incubated at 37° C., 160 rpm overnight. Aliquots of overnight cultures were inoculated into 50 ml of fresh broth media, and incubated at 37° C., 160 rpm. When the OD reached the target value for each strain (see Table 1), cells were harvested by centrifugation at 5000 rpm for 10 min, and then resuspended in the same fresh broth media at the same volume before the centrifugation. Aliquots (1.1 ml) of each cell suspension were diluted in 200 ml of the same broth media as the bacterial solutions for the MIC test.

TABLE 1

Media, aliquots of overnight culture, and target OD of broth cultures for the preparation of bacterial solutions

| Strains | Agar plate media | Broth Media | Aliquots of Overnight Culture | Target OD |
|---|---|---|---|---|
| Staphylococcus aureus DSMZ 1104 | TSA | MH | 1 ml | 0.7-0.9 |
| Staphylococcus haemolyticus ATCC 114126 | TSA | MH | 1 ml | 0.5-0.7 |
| Escherichia coli DSMZ 1103 | TSA[a] | MH[b] | 0.5 ml | 0.3-0.45 |

Note:
[a]TSA, Tryptic Soy Agar (BD Cat No. 236950), [b]MH, Mueller Hinton Broth (BD Cat No. 211443), [c]WC, Wilkins-Chalgren (OXOID Cat No. CM0643).

Preparation of test sample solutions: Sample solutions of 4-methyl-2-pentyl-pyridine and reference material (N302) were prepared as follows. Stock solutions of 1% and 20% were prepared in ethanol, and then seven serial dilutions of each stock solution were prepared in ethanol to obtain a total of 16 solutions of 4-methyl-2-pentyl-pyridine or the reference material. Aliquot (10 µl) of each solution was used for MIC test. The tested final concentrations of each material were 29, 44, 66, 99, 148, 222, 333, 500, 590, 900, 1300, 2000, 3000, 4500, 6700, 10000 ppm. The test material control was trans-hexenal, a known material for MIC tests and control tests (e.g. see Int J Food Microbiol. 2010 Jan. 1; 136(3):304-9.)

MIC test: MIC tests were performed in 96 well plates. Table 2 shows the schematic positions of sample solutions in 96 well plates. Column 1 contained bacterial solution only (the positive growth control), and column 12 contained growth media only (the negative growth control). Aliquots (10 µl) of sample solutions were mixed with 190 µl of bacterial solutions in growth media, at concentrations of $10^5$ to $10^6$ cfu/ml, in wells of the 96 well plates. Three replicates for solution.

The 96 wells plates were incubated at 37° C., 160 rpm overnight. After incubation, wells of 96 well plates were examined. Turbid wells were regarded as an indication of microbial growth.

Minimal inhibition concentration (MIC) was determined as the lowest concentration where no growth was observed. Average MIC values of the three replicates was calculated against each strain (see Table 3).

TABLE 2

Schematic positions of samples in 96 well plates

| A | Positive | | | 590 ppm | 29 ppm | | | 590 ppm | 29 ppm | | | Negative |
|---|---|---|---|---|---|---|---|---|---|---|---|---|
| B | growth | | | 900 ppm | 44 ppm | | | 900 ppm | 44 ppm | | | growth |
| C | control | | | 1300 ppm | 66 ppm | | | 1300 ppm | 66 ppm | | | control (no |
| D | | | | 2000 ppm | 99 ppm | | | 2000 ppm | 99 ppm | | | contamination) |
| E | | | | 3000 ppm | 148 ppm | | | 3000 ppm | 148 ppm | | | |
| F | | | | 4500 ppm | 222 ppm | | | 4500 ppm | 222 ppm | | | |
| G | | | | 6700 ppm | 333 ppm | | | 6700 ppm | 333 ppm | | | |
| H | | | | 10000 ppm | 500 ppm | | | 10000 ppm | 500 ppm | | | |
| | 1 | 2 | 3 | 4 | 5 | 6 | 7 | 8 | 9 | 10 | 11 | 12 |
| | | | | 4-methyl-2-pentyl-pyridine | | | | trans-hexenal | | | | |

TABLE 3

MIC concentrations (in ppm) of 4-methyl-2-pentyl-pyridine vs various strain of bacteria

| Bacteria | MIC of 4-methyl-2-pentyl-pyridine |
|---|---|
| S. aureus Associated with hygiene | 693 ppm (4-methyl-2-pentyl-pyridine is efficiently active in application) |
| S. haemolyticus Associated with body odor | 745 ± 219 ppm (4-methyl-2-pentyl-pyridine is efficiently active in application) |
| E. coli Associated with hygiene | 444 ± 78.72 ppm (4-methyl-2-pentyl-pyridine is efficiently active in application) |

4-methyl-2-pentyl-pyridine is shown to be an effective antimicrobial ingredient in concentrations compatible with consumer products, as so able to participate to a MOC effect.

Example 3: MOC Activity of Compounds of Formula (I) via Inhibition of Olfactory Receptors Stable cell lines expressing specific human (designated OR) or mouse (designated Olfr) olfactory receptors were used as a screening platform to determine the ability of 4-methyl-2-pentyl-pyridine to inhibit malodor compound induced receptor activity. The table below summarizes the cell lines used.

| Malodor Compound | Olfactory Receptors |
|---|---|
| Butyric acid | Olfr558; OR51E1 |
| p-cresol | Olfr740; Olfr742 |
| DMTS | OR4S2 |
| Indole | Olfr742; Olfr740 |

Figure 4A:
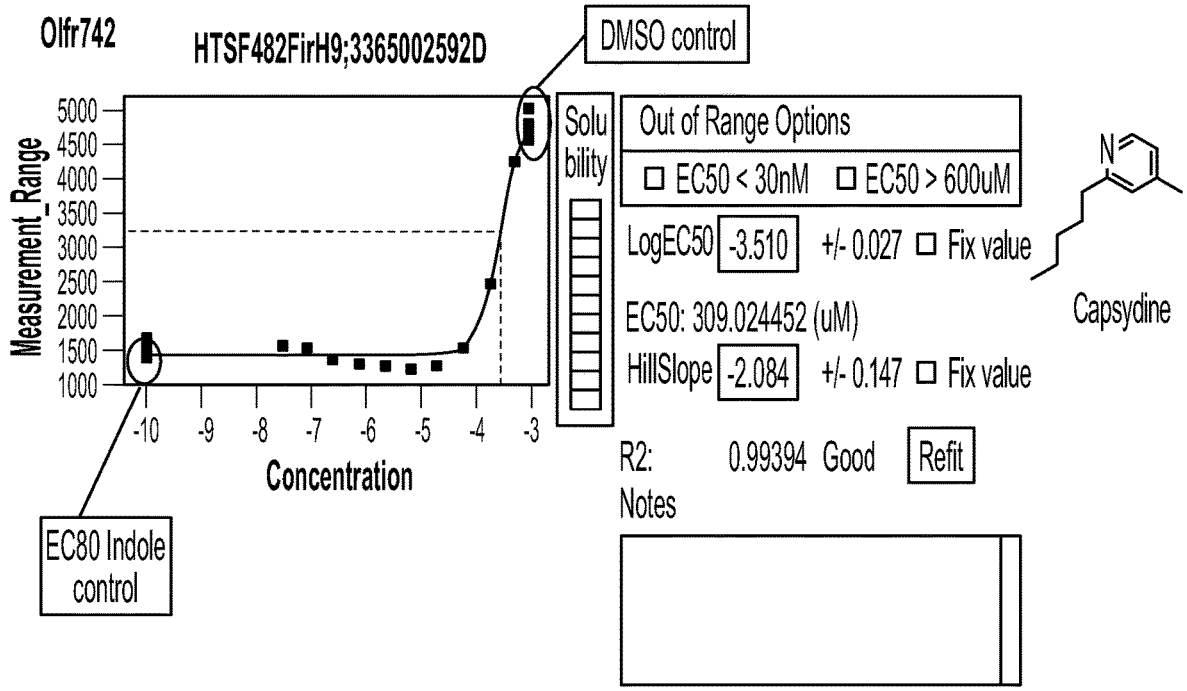
FIG. 4 shows the results of the potency of a compound of formula (I) to inhibit the indole olfactory receptor Olfr742 (panel a), and Olfr740 (panel b).
Figure 4B:
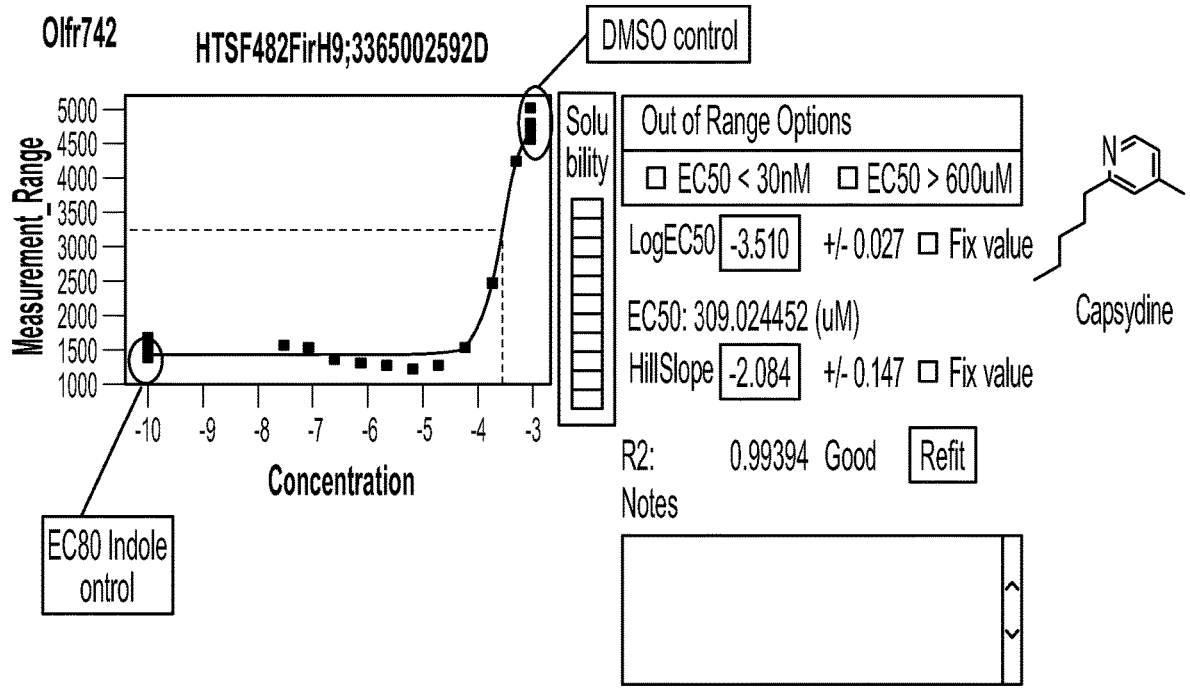

Referring to FIGS. 1-4, a dose-dependent decrease of receptor activity was recorded with increasing concentrations of 4-methyl-2-pentyl-pyridine in the presence of a single activating concentration of either butyric acid (FIG. 1), p-cresol (FIG. 2), DMTS (FIG. 3), or indole (FIG. 4). The $EC_{50}$ values are reported in the table below:

| Malodor Compound | $EC_{50}$ for 4-methyl-2-pentyl-pyridine (μM) | $EC_{50}$ for 4-methyl-2-pentyl-pyridine (μM) |
|---|---|---|
| Butyric acid | Olfr558: 154.29 | OR51E1: Weak |
| p-cresol | Olfr740: 95.82 | Olfr742: 173.38 |
| DMTS | OR4S2: 90.28 | |
| Indole | Olfr742: 309.02 | Olfr740: 164.78 |

4-methyl-2-pentyl-pyridine is shown to be an effective olfactory receptor antagonist in concentrations compatible with consumer products, as so able to participate to a MOC effect. The concentrations used in the assay equate to concentrations ranging from 10 to 100 ppm.

Figure 5:
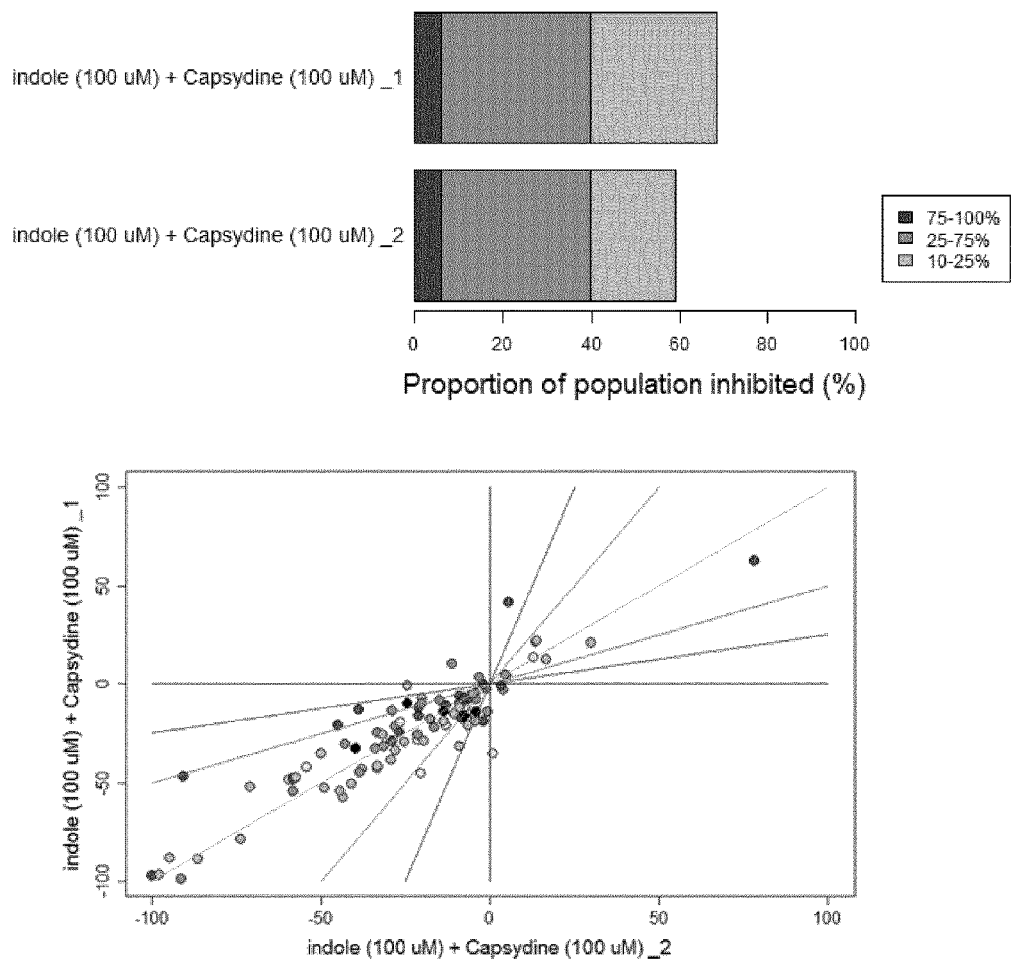
FIG. 5 shows results of live neuron assay antagonism screening against an indole malodor target.
Figure 6:
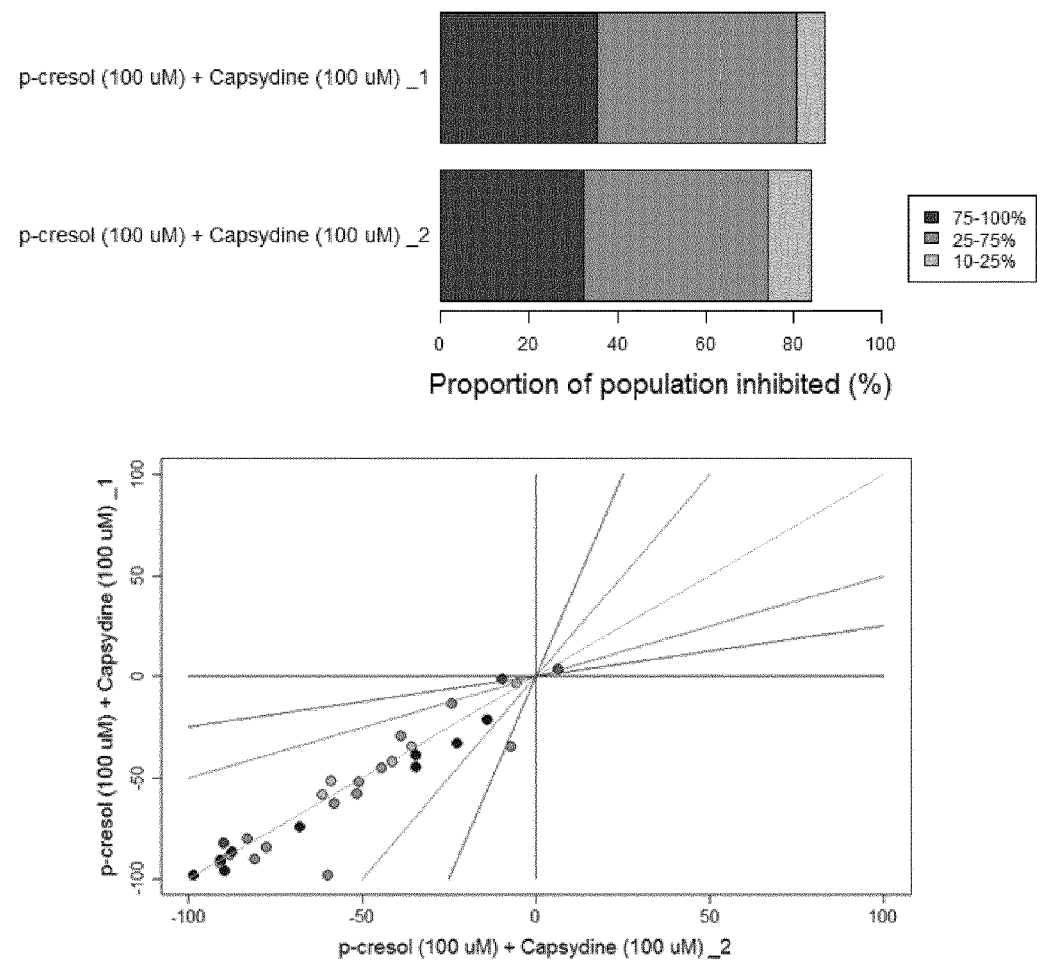
FIG. 6 shows results of live neuron assay antagonism screening against a p-cresol malodor target.
Figure 7:
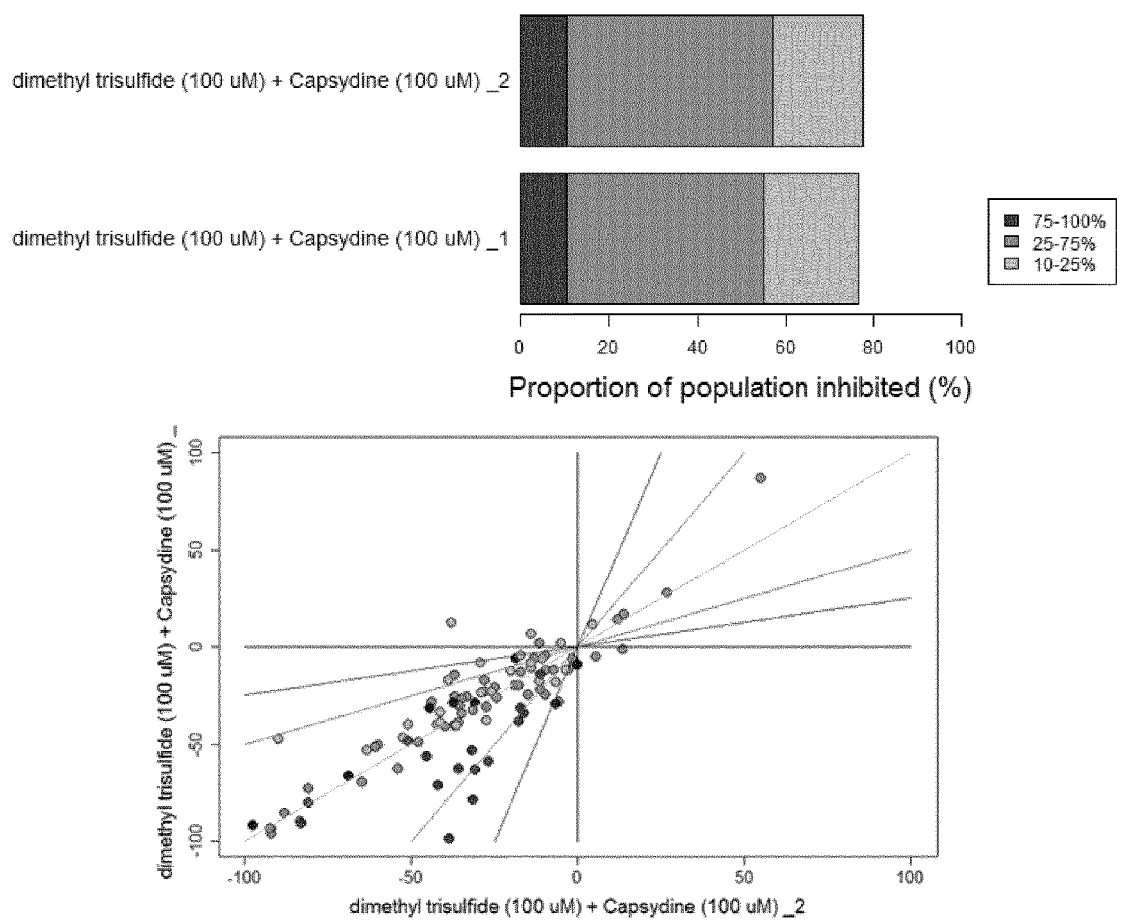
FIG. 7 shows results of live neuron assay antagonism screening against a DMTS malodor target.

Example 4: MOC Activity of Compounds of Formula (I) Determined Using an Ex Vivo Live Neuron Assay In the ex vivo live neuron assay, olfactory sensory neurons (OSNs) are extracted from the olfactory epithelium of mice and can be tested for responses to sequentially delivered stimuli, where responses are detected through live-cell calcium-imaging microscopy. At least 1000 and approximately 5000-10000 OSNs were tested. It has been established through prior research in the field that the vast majority of extracted OSNs express 1 out of the approximately 1200 odorant receptors (ORs) present in the genome of a mouse, such that in our samples of extracted OSNs, the majority of the 1200 ORs should have been represented in at least one OSN. Since the responses of the OSNs to the delivered stimuli are entirely driven by the expressed OR, the OSNs selectively detect and collectively encode the identity and intensity of odorants. By stimulating the OSNs with malodor molecules and measuring the response of each OSN, the subset in which a response is induced is those that detect and therefore presumably encode the malodor molecules. By subsequently delivering a mixture of malodor molecules and a candidate antagonist to the same cells, the degree of suppression of signal in each malodor molecule-responsive OSN can be determined ("level of inhibition"). The degree of inhibition in each cell was binned into one of three groups: low inhibition (10-25%), medium inhibition (25-75%) and strong inhibition (75-100%). In addition, the proportion of malodor molecule-responsive OSNs displaying low, medium and high inhibition was calculated. Examples of these data are shown in FIGS. 5 to 7. Compounds that inhibited greater than a minimum proportion of OSNs at a minimum strength were considered antagonist "hits" and putative malodor suppressing compounds. The minimum levels were, respectively, 10% of the population showing strong inhibition and/or 25% of the population showing medium inhibition and/or 40% of the population showing weak inhibition.

The genetic similarity between mouse and human receptors, due to their shared evolutionary history and presumably similar natural odor environments over evolutionary timescales leads us to suppose that overall observations on malodor compound-responsive populations of mouse ORs should positively correlate with what would be obtained from human ORs, even if individual orthologous receptors (i.e. those believed to share a common ancestor and typically the most similar in genetic sequence) may show varying levels of functional similarity to those form mouse.

FIGS. 5-7 show examples of results from live neuron assay antagonism screening against target fecal malodor compounds, providing evidence of antagonism of malodor receptors. Inhibition levels for the population of neurons were binned into high (75-100%, red), medium (25-75%, blue) and low (10-25%, grey). Compounds considered antagonists or "hits" were required to pass the population quantities denoted by the vertical lines (A, B, C) where the high inhibition must have passed A (10% of population of indole-responsive OSNs), and/or the medium inhibition must have passed B (25% of population of indole-responsive OSNs) and/or the low inhibition must have passed C (40% of population of indole-responsive OSNs).

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

The invention claimed is:

1. A method, wherein the method reduces, prevents, or inhibits a subject's perception of malodor from a malodor source comprising at least one bacterium selected from the group consisting of *S. aureus*, *S. haemolyticus*, and *E. coli*, the method comprising contacting the subject with a malodor counteracting composition comprising
   4-methyl-2-pentylpyridine in an amount sufficient to reduce, prevent, or inhibit the subject's perception of malodor,
   wherein the amount sufficient to reduce, prevent, or inhibit the subject's perception of malodor is from 30 ppm to 300 ppm; and
   wherein the 4-methyl-2-pentylpyridine in an amount sufficient to reduce, prevent, or inhibit the subject's perception of malodor possesses fruity and/or smoky odor notes.

2. The method of claim 1, wherein the malodor is selected from the group consisting of kitchen, laundry, bathroom, tobacco, pet, and body malodor.

3. The method of claim 1, wherein the amount sufficient to reduce, prevent, or inhibit the subject's perception of malodor inhibits, reduces, or decreases the activity of an olfactory receptor specific for a malodor compound.

4. The method of claim 1, wherein the amount sufficient to reduce, prevent, or inhibit the subject's perception of malodor inhibits an olfactory malodor receptor in the subject.

5. The method of claim 1, wherein the amount sufficient to reduce, prevent, or inhibit the subject's perception of malodor is from 30 ppm to 100 ppm.

\* \* \* \* \*